US008535337B2

(12) United States Patent
Chang et al.

(10) Patent No.: US 8,535,337 B2
(45) Date of Patent: Sep. 17, 2013

(54) PEDICLE SCREW INSERTION SYSTEM AND METHOD

(76) Inventors: David Chang, Rochester, NY (US); Nicholas Ransom Powley, St. Paul, MN (US); Alan Fischer, Ames, IA (US); Andrew G. Fischer, Hopkins, MN (US)

(*) Notice: Subject to any disclaimer, the term of this patent is extended or adjusted under 35 U.S.C. 154(b) by 269 days.

(21) Appl. No.: 13/094,527

(22) Filed: Apr. 26, 2011

(65) Prior Publication Data

US 2012/0022544 A1 Jan. 26, 2012

Related U.S. Application Data

(60) Provisional application No. 61/328,062, filed on Apr. 26, 2010.

(51) Int. Cl.
*G01T 1/161* (2006.01)
*H05G 1/06* (2006.01)
*H05G 1/00* (2006.01)
*H05G 1/10* (2006.01)
*H05G 1/24* (2006.01)

(52) U.S. Cl.
USPC ... 606/130; 606/97; 250/363.02; 250/363.07; 378/102

(58) Field of Classification Search
USPC .............. 378/102; 606/97, 130; 250/363.02, 250/363.07
See application file for complete search history.

(56) References Cited

U.S. PATENT DOCUMENTS

| | | | |
|---|---|---|---|
| 4,282,438 A * | 8/1981 | Nishida et al. ................ | 378/11 |
| 5,013,317 A | 5/1991 | Cole | |
| 5,390,225 A * | 2/1995 | Hawman ........................... | 378/6 |
| 5,772,594 A | 6/1998 | Barrick | |
| 6,021,343 A | 2/2000 | Foley | |
| 6,092,928 A | 7/2000 | Mattson | |
| 6,214,013 B1 | 4/2001 | Lambrecht | |
| 6,285,902 B1 | 9/2001 | Kienzle | |
| 6,342,056 B1 | 1/2002 | Mac-Thiong | |
| 6,478,802 B2 * | 11/2002 | Kienzle et al. ................ | 606/130 |
| 6,520,969 B2 | 2/2003 | Lambrecht | |
| 6,574,493 B2 | 6/2003 | Rasche | |
| 6,587,710 B1 * | 7/2003 | Wainer .......................... | 600/427 |

(Continued)

OTHER PUBLICATIONS

Notification of Transmittal of the International Search Report and the Written Opinion of the International Searching Authority or the Declaration, International Application No. PCT/US2011/033985, mailed Nov. 25, 2011, 8 pages.

(Continued)

*Primary Examiner* — Kevin T Truong
*Assistant Examiner* — David Bates
(74) *Attorney, Agent, or Firm* — Patterson Thuente Pedersen, P.A.

(57) ABSTRACT

Improved methods and apparatuses for inserting pedicle screws in accordance with embodiments of the present invention include an image correction algorithm. In various embodiments, an original image of a region of interest of a patient including a pedicle is created with an X-ray emitter and an X-ray detector. Due to the X-ray emitter not being aligned orthogonal to the X-ray detector, the original image will be skewed. Using a known location and orientation of the X-ray detector, a location and orientation of the X-ray emitter provided by a position monitoring system, and the original image, a processing system can execute the image correction algorithm to provide a corrected image to allow a surgeon to properly insert a pedicle screw along the axis of the pedicle while viewing an accurate corrected image in real time.

23 Claims, 7 Drawing Sheets

(56) References Cited

U.S. PATENT DOCUMENTS

| | | |
|---|---|---|
| 6,697,664 B2 | 2/2004 | Kienzle |
| 6,877,863 B2* | 4/2005 | Wood et al. .................. 353/70 |
| 6,887,245 B2* | 5/2005 | Kienzle et al. ................ 606/80 |
| 6,917,827 B2 | 7/2005 | Kienzle |
| 6,920,347 B2 | 7/2005 | Simon |
| 7,022,082 B2* | 4/2006 | Sonek .......................... 600/461 |
| 7,110,807 B2 | 9/2006 | Webber |
| 7,235,076 B2 | 6/2007 | Pacheco |
| 7,314,048 B2* | 1/2008 | Couture et al. ............... 128/898 |
| 7,826,889 B2* | 11/2010 | David et al. .................. 600/436 |
| 8,126,114 B2* | 2/2012 | Naylor et al. ................. 378/65 |
| 8,182,491 B2* | 5/2012 | Selover et al. ................ 606/104 |
| 8,350,893 B2* | 1/2013 | Lee et al. ..................... 348/49 |
| 8,366,719 B2* | 2/2013 | Markey et al. ............... 606/104 |
| 2001/0046034 A1* | 11/2001 | Gold et al. .................... 353/72 |
| 2003/0130576 A1* | 7/2003 | Seeley et al. ................. 600/426 |
| 2005/0143654 A1 | 6/2005 | Zuiderveld |
| 2005/0154295 A1 | 7/2005 | Quistgaard |
| 2006/0106400 A1 | 5/2006 | Fernandez |
| 2006/0293592 A1 | 12/2006 | Jensen |
| 2007/0270877 A1 | 11/2007 | Park |
| 2008/0109013 A1* | 5/2008 | Fu et al. ....................... 606/130 |
| 2008/0119728 A1 | 5/2008 | Frenkel |
| 2008/0277591 A1* | 11/2008 | Shahar et al. ................. 250/394 |
| 2011/0295109 A1 | 12/2011 | Lavallee |
| 2012/0022544 A1* | 1/2012 | Chang et al. .................. 606/97 |

OTHER PUBLICATIONS

Akiyama et al., "Computer-Assisted Fluoroscopic Navigation System for Removal of Distal", www.lexis.com, dated Apr. 2007, 4 pages.

Shoham et al., "Bone-Mounted Miniature Robot for Surgical Procedures: Concept and Clinical Applications", *IEEE*, dated Oct. 2003, pp. 893-901, vol. 19.

Hiroyuki et al., "Technical note; The Accuracy and Safety of Image-Guidance System Using Intraoperative", www.lexis.com, dated Mar. 2003, 8 pages.

Santos-Munne et al., "A Stereotactive/Robotic System for Pedicle Screw Placement", *Interactive Technology and the New Paradigm for Healthcare* (Proceedings of the Medicine Meets Virtual Reality III Conference, San Diego, 1995), dated Jan. 1995, pp. 326-333.

Application and File History for U.S. Appl. No. 13/094,524, filed Apr. 26, 2011, Inventors: Chang et al.

International Preliminary Report on Patentability, Application No. PCT/US2011/033985, mailed Nov. 8, 2012, 5 pages.

* cited by examiner

PEDICLE SCREW INSERTION SYSTEM AND METHOD

RELATED APPLICATION

The present application claims the benefit of U.S. Provisional Application No. 61/328,062, filed Apr. 26, 2010, the disclosure of which is hereby incorporated by reference.

FIELD OF THE INVENTION

The present invention relates to apparatuses and methods for inserting pedicle screws. More specifically, the present invention relates to a pedicle screw drill system and method that utilizes x-ray imaging to place pedicle screws along the axis of the pedicles when the x-ray source is not orthogonal to the base.

BACKGROUND OF THE INVENTION

Pedicle screw fixation is an increasingly important technique in spine surgery. Pedicle screws are inserted into the vertebrae or spinal column of a patient in order to make it possible for a spinal column of a patient suffering from a traumatic or degenerative disease to perform its proper function. Accurate placement of pedicle screws is vital to avoid iatrogenic injuries to nervous or vascular structures. Accurate placement of the screws in the vertebral body also yields greater bony purchase, therefore increasing pull out strength. Currently, there are a number of methods used to insert pedicle screws into the spine of a patient.

One method of inserting pedicle screws involves blind placement of the screws by a physician. The physician, guided only by sight, drills the holes based on the physician's experience and knowledge of the spine. Such a technique can be effectively practiced only by highly skilled and experienced practitioners and is generally considered a wholly inadequate and not recommended procedure.

Intra-operative navigations systems such as, for example, the Medtronic StealthStation® and Stryker® Navigation Systems, are also used for placement of pedicle screws. These systems provide markers and other structures to guide the physician's drilling process. However, such systems are expensive, add significant time to the surgical procedure due to setup, and can suffer from intra-operative shifting of structures and registration error.

Another technique for placement of pedicle screws utilizes traditional fluoroscopic x-ray techniques. This involves the use of standard x-ray systems, such as C-arms, to image the target pedicle area as the physician drills. Such systems are economical and provide real time data which eliminates intra-operative shift of structures and registration errors. However, they are typically limited to use with anterior-posterior and lateral projections. These systems are also suboptimal when the pedicle sits at angles that are not orthogonal to the base of the X-ray system. In addition, C-arm x-ray systems are large and cumbersome, so repositioning for a procedure can be a lengthy process.

It would be desirable to provide an X-ray directed pedicle screw drill system designed to replace existing methods for drilling pedicle screws with a faster and more accurate system that exposes the patient to a minimal amount of X-ray radiation

SUMMARY OF THE INVENTION

Improved methods and apparatuses for inserting pedicle screws in accordance with embodiments of the present invention include an image correction algorithm. In various embodiments, an original image of a region of interest of a patient including a pedicle is created with an X-ray emitter and an X-ray detector. Due to the X-ray emitter not being aligned orthogonal to the X-ray detector, the original image will be skewed. Using a known location and orientation of the X-ray detector, a location and orientation of the X-ray emitter provided by a position monitoring system, and the original image, a processing system can execute the image correction algorithm to provide a corrected image to allow a surgeon to properly insert a pedicle screw along the axis of the pedicle while viewing an accurate corrected image in real time.

In one embodiment, a system for inserting a pedicle screw into a pedicle of a patient utilizes an image correction algorithm. System can include a manually positionable X-ray emitter including a drill assembly for inserting the pedicle screws. An X-ray detector can detect the X-rays from the X-ray emitter and generate an original image of a region of interest between the X-ray emitter and X-ray detector including the pedicle. A position monitoring system can monitor a position and orientation of the X-ray emitter. A processor operably connected to the position monitoring system and the X-ray detector can execute an image correction algorithm operable to provide a corrected image from the original image due to the original image being skewed as a result of the X-ray emitter not being perpendicular to the X-ray detector. A video display can display the corrected image in real-time to a surgeon performing an operation to insert the pedicle screw into the pedicle of the patient.

In another embodiment, a method includes providing a system for inserting a pedicle screw into a pedicle of a patient. The system can include a manually positionable X-ray emitter including a drill assembly, an X-ray detector that detects the X-rays from the X-ray emitter, a position monitoring system that monitors a position and orientation of the X-ray emitter, a processor that executes an image correction algorithm and a video display. The method can further include instructions for inserting the pedicle screw into the pedicle of the patient. The instructions can include manually positioning the X-ray emitter in more than three degrees of freedom at an insertion angle that is axially aligned with the pedicle and that is not perpendicular to the X-ray detector to obtain an original image of a region of interest including the pedicle, which results in the original image being skewed. The instructions further comprise viewing a corrected image of the region of interest on the video display that result from application of the image-correction algorithm to the skewed original image and inserting the pedicle screw with the drill assembly while viewing the corrected image in real-time.

The above summary of the various embodiments of the invention is not intended to describe each illustrated embodiment or every implementation of the invention. This summary represents a simplified overview of certain aspects of the invention to facilitate a basic understanding of the invention and is not intended to identify key or critical elements of the invention or delineate the scope of the invention.

BRIEF DESCRIPTION OF THE DRAWINGS

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE DRAWINGS

In the following detailed description, numerous specific details are set forth in order to provide a thorough understanding of the present invention. However, one skilled in the art will recognize that the present invention may be practiced without these specific details. In other instances, well-known methods, procedures, and components have not been described in detail so as to not unnecessarily obscure aspects of various embodiments of the present invention.

Figure 1:
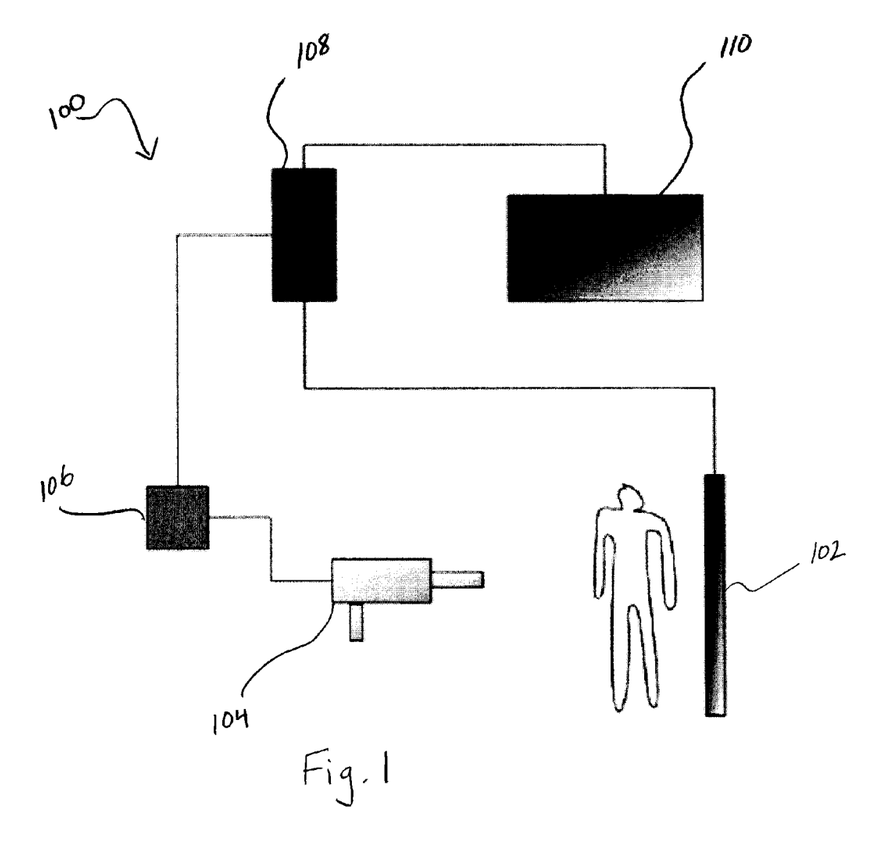
FIG. 1 depicts a pedicle screw insertion system according to an embodiment of the present invention.

Referring to FIG. 1, a schematic representation of a pedicle screw insertion system 100 according to an embodiment of the present invention is depicted. System 100 generally includes an X-ray emitter 104 and an X-ray detector 102 for detecting the X-rays generated by emitter 104. X-ray emitter 104, as described more fully herein, can also incorporate a drill for inserting pedicle screws into the spine of a patient. System 100 can also include a position monitoring system 106 to track or sense the movements of the emitter 104 in any number of degrees of freedom. A processor executing a computer-implemented image correction algorithm 108 can be used, as described more fully herein, to provide a more accurate image of the X-rayed region to a surgeon, who views the corrected image on a monitor or display 110 in real-time.

The X-ray detector 102 is placed beneath/opposite the patient in the area of interest, i.e., the area where pedicle screws are going to be placed. In one embodiment, X-ray detector 102 is a planar flat-panel detector mounted beneath the patient table and on an X/Y movable stage allowing it to be positioned under the area of interest of the patient as needed. Such modern flat-panel detectors are advantageous in that they are light weight, can run high frame-rates, use fewer parts and can provide an immediate digital image. Various flat-panel X-ray detectors that can be used with embodiments of the present invention are manufactured by Varian Medical Systems of Palo Alto, Calif.

In one embodiment, detector 102 provides at least near real-time feedback to the surgeon. In this embodiment, detector 102 can acquire images at a frame rate of at least 15 frames per second. It has been observed that at rates of higher than 25 frames per second it is difficult to discern meaningful differences in detected images as a result of such higher rates, so a range of frame rates of 15 frames per second to 25 frames per second is preferred. Ideally, the system 100 uses the largest flat-panel detector 102 that can provide such a response time in the desired range of frame rates. In one embodiment, such response times can be provided by a 16" by 12" detector 102.

The X-ray emitter 104 can be a handheld X-ray gun that can include an X-ray source, such as an X-ray tube having an anode, a cathode, and a power source, located behind an actuator for inserting pedicles screws into a spine of a patient, such as a drill bit and drive assembly. In one embodiment, the drill bit and drive mechanism, such as a planetary gear system, are X-ray translucent so as not to interfere with the emitted x-rays. In this embodiment, at least the portion of the drill assembly that is coaxial with an axis of insertion of the pedicle screw is X-ray translucent. This provides an unobstructed image as the screw is inserted, which allows the surgeon to image the target at the same time as drilling for the screw without the need for a separate X-ray device. One embodiment of an X-ray translucent drill mechanism, aspects of which can be used in embodiments of the present invention, is disclosed in U.S. Pat. No. 5,013,317 to Cole et al., which is incorporated herein by reference. In another embodiment, drill assembly can be aligned to operate on an axis that is parallel to, but does not overlap with, the axis along which the X-rays are emitted, so as not to be positioned between the X-ray emitter and detector while still being aligned at the same angle.

Figure 3A:
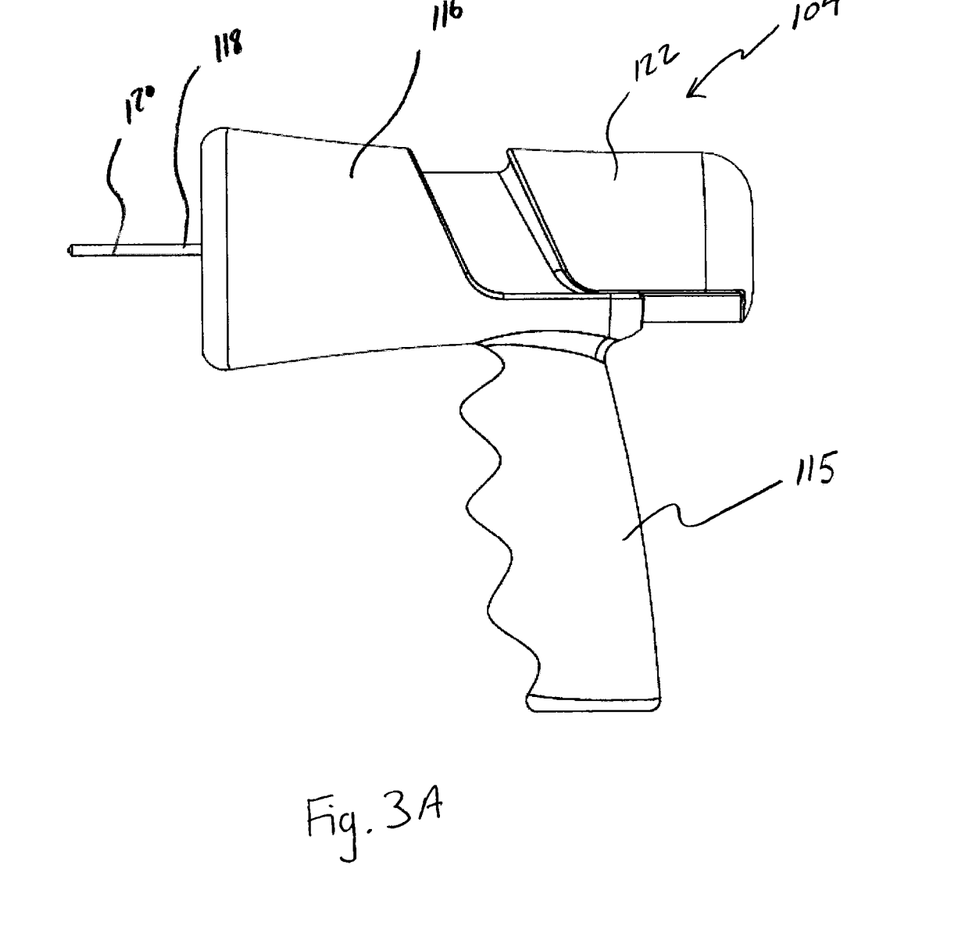
FIG. 3A depicts an X-ray emitter gun according to an embodiment of the present invention.
Figure 3B:
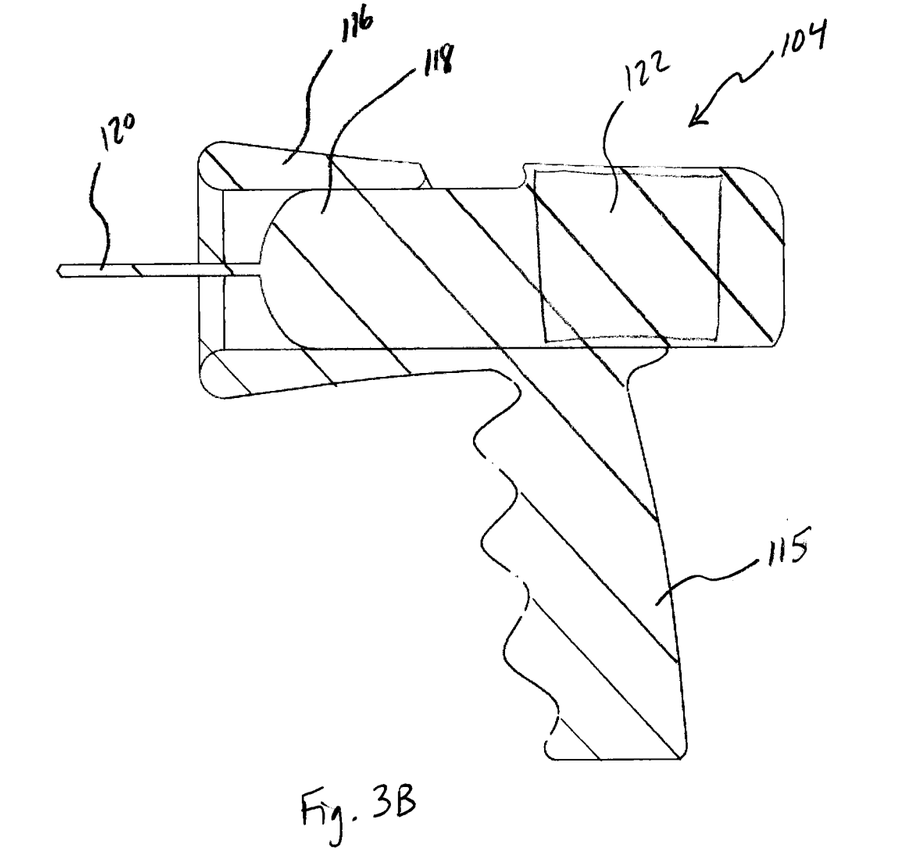
FIG. 3B is a cross-sectional view of the X-ray emitter gun of FIG. 3A, taken at the midplane of the gun looking into the page.

An X-ray emitter 104 in the form of a handheld X-ray drill gun according to an embodiment of the present invention is depicted in FIGS. 3A and 3B. X-ray gun 104 is lightweight and easily maneuverable by a surgeon and includes a handle 115 connected to a housing 116. Housing contains a drill mechanism 118, which as noted above can by X-ray translucent, and an X-ray source 122. In one embodiment, the X-ray source is positioned behind the drill mechanism 118 in the housing. Drill mechanism 118 can be provided with variously sized interchangeable drill bits 120 that can form pilot holes in the pedicles. Drill mechanism 118 can insert the pedicle screws into the pilot holes or can directly insert pedicle screws without first forming pilot holes. In some embodiments, X-ray gun 104 can be about the size of a modern cordless drill, allowing the surgeon to move about freely with the device in order to locate the axis of the pedicle. In one embodiment, X-ray emitter can be provided with a safety feature that only allows X-rays to be emitted when it is aimed at the detector, to prevent unnecessary and potentially harmful emission of X-rays.

A position monitoring system 106 is used in system 100 because proper visualization of the procedure requires knowing where the X-ray emitter 104 is positioned and oriented in space. In some embodiments, the detector 102 does not need to be tracked by the position monitoring system 106 because it maintains a fixed orientation in space after initially being set for the procedure, so its location and orientation are known. In other embodiments, the surgeon can adjust the detector 102 during the procedure so its location and orientation can also be tracked.

Position monitoring system 106 must be compatible with a nearby X-ray source, tolerant of significant metal in the environment, and have high reliability and accuracy. In some embodiments, position monitoring system 106 can be an optical tracking system, such as manufactured by Ascension Technology Corporation of Milton, Vt. In other embodiments, positioning monitoring system 106 can be a kinematic/mechanical tracking via an arm or linkage. In such an embodiment, the X-ray emitter/gun can be attached to a manually positionable arm anchored to a ceiling, wall or floor of an operating room or a movable base in the operating room. In other embodiments, position monitoring system can use radio-frequency identification, image analysis using infrared light, or other wireless tracking/sensing. In some embodiments, some or all of position monitoring system 106 can be incorporated into X-ray emitter 104 rather than being a separate system. In such embodiments, position monitoring system 106 can use one or more of accelerometers, gravitometers, magnetometers, and global positioning systems to track and/or sense the location and orientation of emitter 104. Position monitoring system 106 can allow the emitter to be positionable, and track the positioning of the emitter, in at least three or more degrees of freedom. In some embodiments, the emitter can be positionable in five or six degrees of freedom. In one embodiment, emitter can be lockable to prevent movement in one or more degrees of freedom for all or part of the procedure, such as only allowing the emitter to be moved along the axis of insertion once proper alignment has been obtained.

Tracking the X-ray emitter's 104 location and orientation relative to the detector 102 and imaged area allows the use of a perspective image correction algorithm to eliminate the need to keep the gun perpendicular to the plate, giving the surgeon a great deal of freedom of movement in inserting pedicle screws. This is desirable because the pedicle is often not aligned perpendicular to the detector and each pedicle may have a different alignment. To properly place pedicle screws, the pilot hole must be accurately drilled axially down the pedicle. However, aligning the emitter/drill 104 axially with the pedicle causes it to be at angle to the detector 102, which results in a skewed image being detected and generated by the detector. Use of an image correction algorithm allows the surgeon to align the X-ray gun at an angle to the detector that is perpendicular to the pedicle (regardless of the alignment of the pedicle relative to the detector) for inserting the pedicle screw while visualizing an accurate image of the pedicle.

Figure 2:
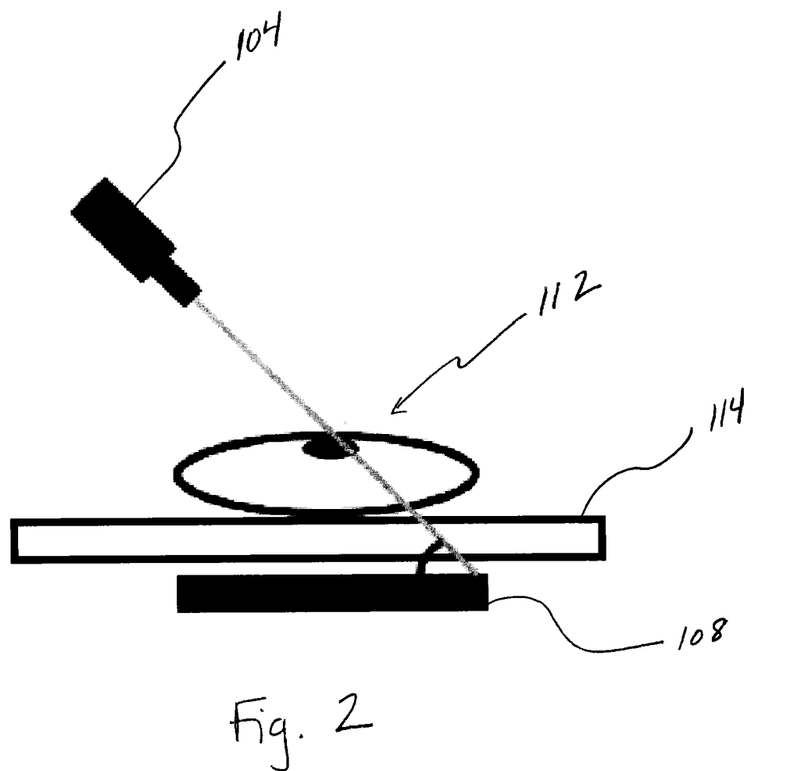
FIG. 2 depicts a pedicle screw insertion system according to an embodiment of the present invention.

The image correction algorithm 108 therefore allows the X-ray emitter 104 to be used in alignments that are not orthogonal to the X-ray detector 102 when the emitter 104 is being used to image the area of interest 112 of the patient on the patient table 114, as depicted in FIG. 2. The skewed image resulting from non-orthogonal alignment of the emitter 104 and detector 102 can typically result in misaligned pilot holes (i.e., not axially aligned) for the pedicle screws. The image correction algorithm 108 corrects this skewed image so that a true image is shown to the surgeon in real time, allowing for more accurate placement of pedicle screws. It should also be noted, as can be seen in FIG. 2, that the thickness of the table 114 combined with the thickness of the patient 112 places a geometric limit on the angle at which the X-ray emitter 104 can be used relative to the area of interest 112 in order to be captured by the detector 102.

Figure 4:
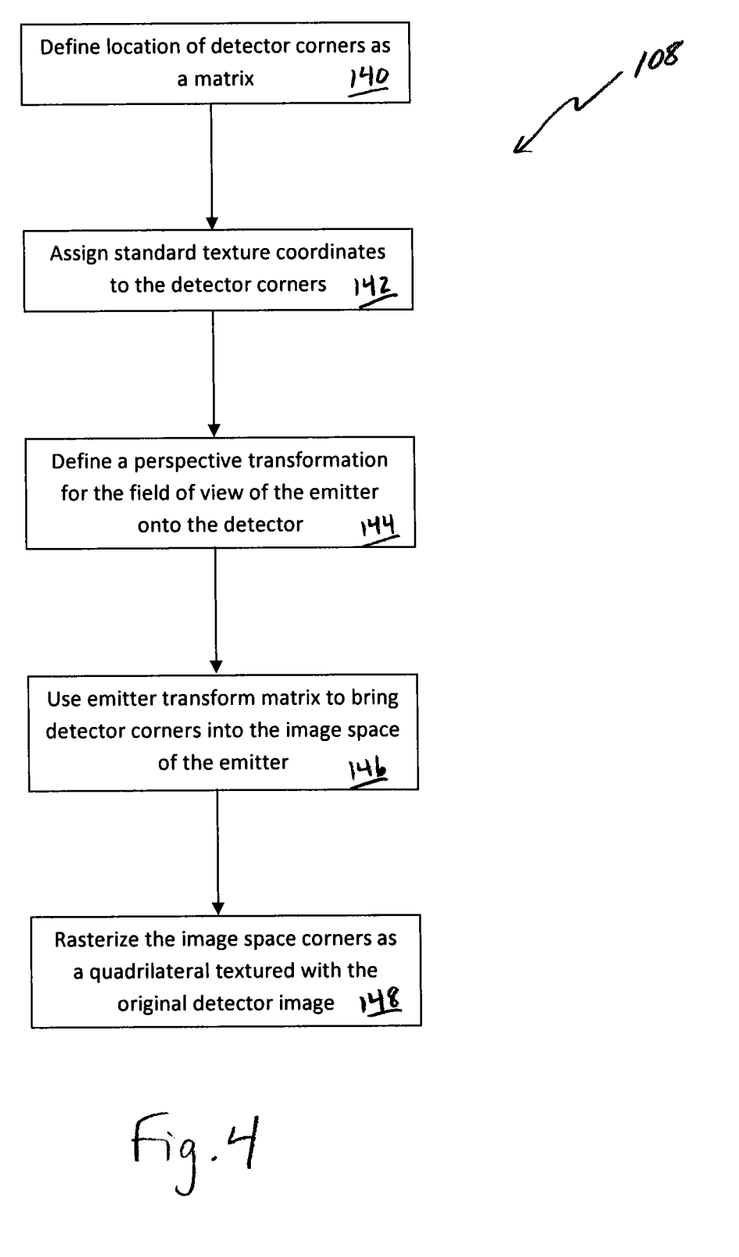
FIG. 4 depicts a flowchart of steps of an image correction algorithm according to an embodiment of the present invention.

In one embodiment as shown in FIG. 4, the image correction algorithm 108, which can be executed by a processor, operates directly on the texture coordinates of the original image recorded by the detector 102 using matrix transforms. Transform matrices are a consistent way of representing linear transforms in a computational format. By representing object locations as vectors, e.g., $f=(x, y, z)$, those objects may be transformed in space (to f') by multiplying them with a transform matrix T such that $f'=Tf$. If the detector 108 dimensions and it's transform in space D are known, the location of the four corners of the detector 102 can be defined with these methods at step 140 in a single 4×4 matrix C, where x1, y1 and z1 (obtained from D and detector 102 geometry) are a first corner of the detector 102 and so on up to x4, y4 and z4. The fourth element of each corner's vector represents the scale of each vector, which may be set to 1.

$$C = \begin{bmatrix} x1 & x2 & x3 & x4 \\ y1 & y2 & y3 & y4 \\ z1 & z2 & z3 & z4 \\ 1 & 1 & 1 & 1 \end{bmatrix}$$

Standard texture coordinates ranging from 0 to 1 can then be assigned to the four corner points at step 142. Texture coordinates (or UV coordinates) are a tool used to linearly map a two-dimensional image onto a three-dimensional object in space. These coordinates, usually represented as u and v, are assigned across an image, ranging from 0 to 1 in each direction. Each vertex of the three-dimensional object is assigned a u and v coordinate indicating which part of the two-dimensional image is associated with that vertex. Since the detector plate is rectangular and is covered by the detected image, the four corners (or vertices) of the detector map correspond to the four corners of the detected image. These four texture coordinates are packed into a texture matrix T.

$$T = \begin{bmatrix} 0 & 1 & 1 & 0 \\ 0 & 0 & 1 & 1 \end{bmatrix}$$

By treating the X-ray emitter 104 as something of an imaginary camera, a perspective transformation for the field of view ("fov") onto the detector 102 can be defined using a standard perspective transform matrix at step 144. Preferably, the fov is computed to be just large enough to view the whole detector plate from the emitter's location. In most applications, a field of view of 45 degrees is sufficient. A perspective transform matrix alters the shape of a given geometry to match the view of that geometry from a defined location. It adds perspective to the resulting image, such as by causing portions of the geometry that are further away to be smaller. This mimics the view as would be seen by the human eye from the defined location.

$$P = \begin{bmatrix} \frac{1}{h} & 0 & 0 & 0 \\ 0 & \frac{1}{h} & 0 & 0 \\ 0 & 0 & \frac{(far + near)}{(near - far)} & \frac{(2 \; far \; near)}{(near - far)} \\ 0 & 0 & -1 & 0 \end{bmatrix}$$

Where $h=\tan(fov/2)$ and far and near are the distances to the far and near view planes. For optimal viewing, near is set at 1 and far is the distance between the X-ray emitter 104 and the furthest corner of the detector 102. Next, the gun/emitter transform matrix G (obtained from the position monitoring system) can be used to bring the detector 102 corners into the image of the imaginary camera, C*, at step 146.

$$C^* = PGC$$

Finally, the corrected image is obtained at step 148 by rasterizing the image space corners C* as a quadrilateral textured with the original detector image, by interpolating according to the texture coordinates. Rasterization is a standard computer graphics algorithm, which is known to those skilled in the art. Rasterization, also known as scan conversion, is the process of rendering a three-dimensional shape or scene onto a flat two-dimensional surface, usually so it can be viewed on a monitor. Rasterization is used as part of the image correction algorithm 108 to render the transformed detector plate object (textured with its detected image) into the view space of the imaginary camera located at the gun/emitter. This yields the corrected image. In one embodiment, the image correction algorithm is performed by a desktop or laptop computer. In other embodiments, the algorithm can be performed by a processor within the emitter 104 or detector 102 or associated with the monitor or display 110. In one embodiment, the algorithm continuously runs during the operation to provide a continuous real-time corrected image that adjusts for movements of the emitter 104, detector 102 or region of interest.

$$CorrectedImage = Rasterize(C^*, T, OriginalImage)$$

By defining the field of view and near/far planes as described herein, a minimum of information is lost during the image correction process. No scaling is required to obtain a properly sized corrected image. The entire process can also be implemented using modern graphics hardware. Corrected images can therefore be processed at extremely high frame rates on the order of hundreds of times per second even for large images.

Figure 5A:
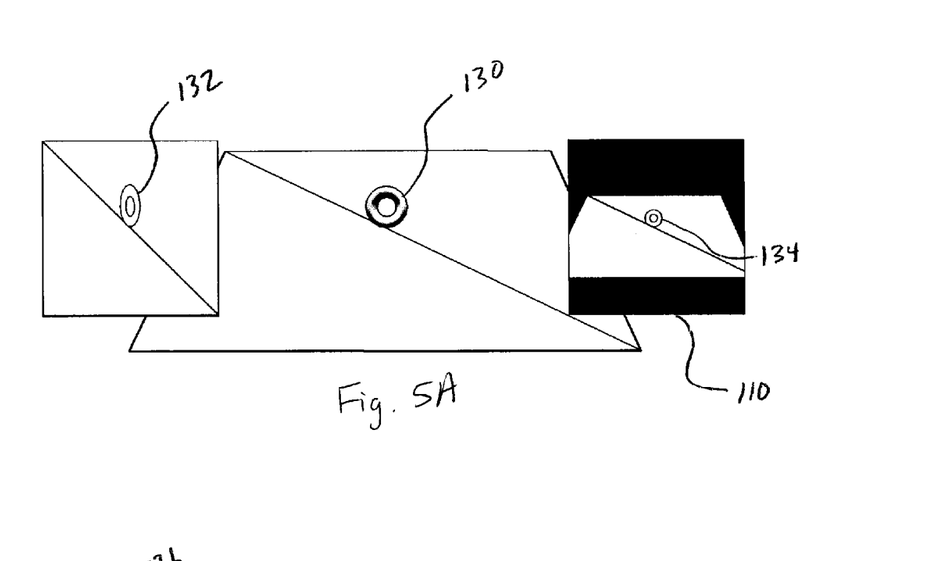
FIG. 5A is a view of an object and original and corrected images of the object according to an embodiment of the present invention.
Figure 5B:
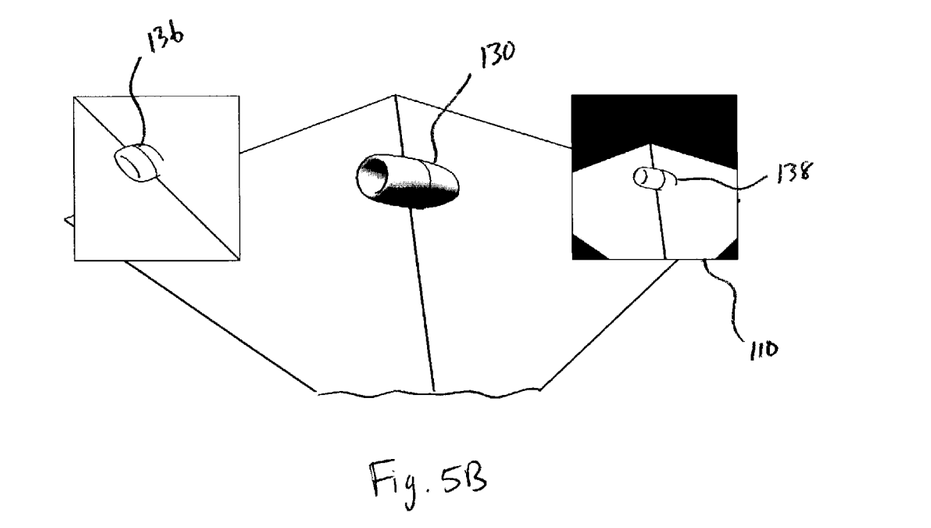
FIG. 5B is another view of an object and original and corrected images of the object according to an embodiment of the present invention.

FIGS. 5A and 5B depict results of such image corrections. In FIG. 5A, a cylindrical object 130 is being viewed with the X-ray emitter 104 along the vertical axis of the object. On the left the original image 132 result as initially detected by the X-ray detector 102 is displayed. Because of the angle between the emitter 104 and the detector 102, the image 132 is skewed. The corrected image 134 as displayed on a monitor 110 following application of the image correction algorithm 108 described herein to the image 132 recorded at the detector, which as can be seen is identical to the actual image 130, is displayed on the right. FIG. 5B depicts a view of a cylindrical object 130 from an oblique angle with the X-ray emitter 104. Similarly, the original image 136 as detected by the X-ray detector 102 is skewed, whereas the corrected image 138 displays the actual appearance of the object 130 from the oblique angle.

Figure 6:
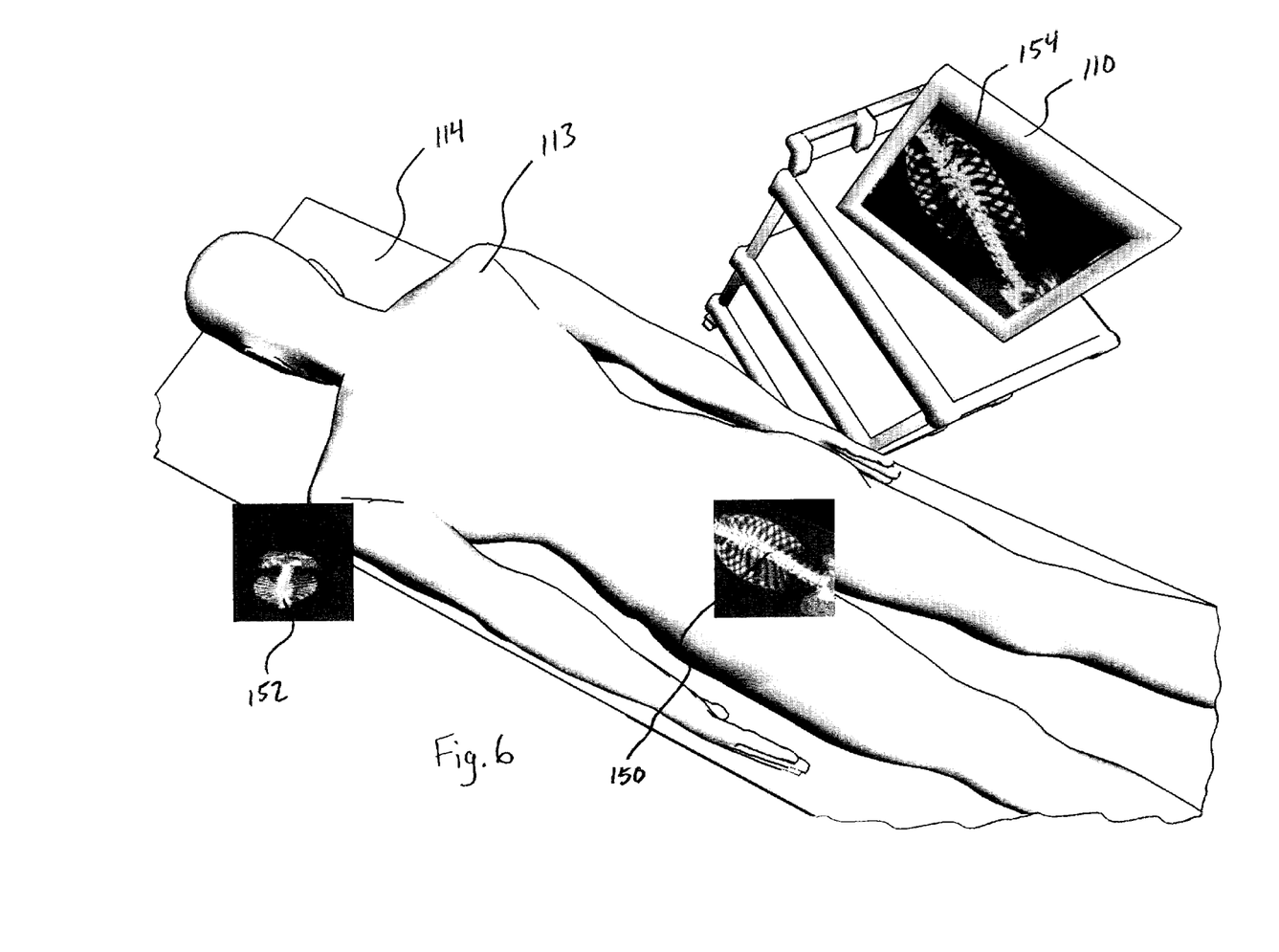
FIG. 6 depicts the use of a pedicle screw insertion system according to an embodiment of the present invention.

Referring now to FIG. 6, there can seen the result of such an image correction during a procedure being performed on a patient 113 on a patient table 114 according to an embodiment of the present invention. The view in the Figure is taken down the emitting axis of an X-ray emitter at an angle to the detector. The original skewed image 152 generated by the detector is corrected with the processor operating the image-correction algorithm and is displayed as a corrected image 154 that shows the actual appearance 150 of the patient's spine/pedicle from the angle on the monitor 110.

The monitor or display 110 need only be safe for use in an operating room and large enough to be easily observed by a surgeon while performing an operation. The monitor must be sterile if located within the sterile field of the procedure. If the monitor is not within the sterile field, it will not have to be sterile but will have to be larger than a monitor within the sterile field in order to be viewable from within the sterile field. In one embodiment, the display can be part of the X-ray emitter gun, such as a video screen located on a proximal end of the gun.

Various embodiments of systems, devices and methods have been described herein. These embodiments are given only by way of example and are not intended to limit the scope of the present invention. It should be appreciated, moreover, that the various features of the embodiments that have been described may be combined in various ways to produce numerous additional embodiments. Moreover, while various materials, dimensions, shapes, implantation locations, etc. have been described for use with disclosed embodiments, others besides those disclosed may be utilized without exceeding the scope of the invention.

The invention claimed is:

1. A system for inserting a pedicle screw into a pedicle of a patient, comprising:
   a manually positionable X-ray emitter adjustable in more than three degrees of freedom, the X-ray emitter including a drill assembly adapted to insert a pedicle screw into a pedicle of a patient along an axis of operation;
   a generally planar X-ray detector that detects the X-rays from the X-ray emitter, the X-rays oriented along an axis parallel to the axis of operation of the drill assembly, wherein the X-ray detector generates an original image of a region of interest that includes the pedicle when positioned between the X-ray detector and the X-ray emitter, and wherein the X-ray emitter is capable of being positioned such that the X-rays are not perpendicular to a plane of the planar X-ray detector;
   a computer controlled position monitoring system that uses a processor to monitor a position and an orientation of the X-ray emitter in the more than three degrees of freedom;
   wherein the processor is operably connected to the position monitoring system and the X-ray detector and configured to execute an image correction algorithm, the image correction algorithm operable to provide a corrected image from the original image, the original image of the pedicle being skewed when the axis along which the X-rays are emitted is at an angle that is not perpendicular to the X-ray detector relative to an actual appearance of the pedicle from the angle and the corrected image showing the actual appearance of the pedicle; and
   a video display linked to the processor to display the corrected image in real-time to a surgeon performing an operation to insert the pedicle screw into the pedicle of the patient.

2. The system of claim 1, wherein the image correction algorithm executed by the processor operates directly on texture coordinates of the original image generated by the X-ray detector using matrix transforms.

3. The system of claim 1, wherein the image correction algorithm executed by the processor utilizes rasterization to provide the corrected image.

4. The system of claim 1, wherein the computer controlled position monitoring system is a kinematic or mechanical tracking system.

5. The system of claim 4, wherein the X-ray emitter is connected to an arm of the kinematic or mechanical tracking system.

6. The system of claim 1, wherein the computer controlled position monitoring system is an optical tracking system.

7. The system of claim 1, wherein the computer controlled position monitoring system is at least partially located within the X-ray emitter.

8. The system of claim 1, wherein the X-ray emitter is manually positionable in at least five degrees of freedom.

9. The system of claim 1, wherein the axis of operation of the drill assembly and the axis along which the X-rays are emitted are coaxial.

10. The system of claim 9, wherein at least a portion of the drill assembly that is coaxial with the axis along which the X-rays are emitted is formed of a material that is X-ray translucent.

11. A method comprising:
  providing a system for inserting a pedicle screw into a pedicle of a patient, the system comprising:
    a manually positionable X-ray emitter adjustable in more than three degrees of freedom, the X-ray emitter including a drill assembly for inserting the pedicle screw along an axis of operation;
    a generally planar X-ray detector that detects the X-rays from the X-ray emitter, the X-rays oriented along an axis parallel to the axis of operation of the drill assembly, wherein the X-ray emitter is capable of being positioned such that the X-rays are not perpendicular to a plane of the planar X-ray detector;
    a computer controlled position monitoring system that uses a processor to monitor a position and an orientation of the X-ray emitter in the more than three degrees of freedom;
    wherein the processor is operably connected to the position monitoring system and X-ray detector such that the processor is configured to execute an image correction algorithm; and
    a video display linked to the computer controlled position monitoring system;
  providing instructions for using the system to insert the pedicle screw into the pedicle of the patient, the instructions comprising:
    manually positioning the X-ray emitter in more than three degrees of freedom and generating an original image of a region of interest that includes the pedicle with the X-ray detector, the X-ray emitter being aligned along the axis of operation of the drill assembly at an angle that is not perpendicular to the X-ray detector resulting in the original image being skewed relative to an actual appearance of the pedicle from the angle;
    viewing a corrected image of the region of interest on the video display showing the actual appearance of the pedicle from the angle, the corrected image resulting from application of the image-correction algorithm to the skewed original image; and
    inserting the pedicle screw into the pedicle of the patient generally axially down the pedicle along the axis of operation with the drill assembly while viewing the corrected image on the video display in real-time.

12. The method of claim 11, wherein the step of manually positioning the X-ray emitter includes moving the X-ray emitter and an arm of a kinematic or mechanical tracking system to which the X-ray emitter is attached.

13. The method of claim 11, wherein the step of manually positioning the X-ray emitter in more than three degrees of freedom includes manually positioning the X-ray emitter in at least five degrees of freedom.

14. A system for inserting a pedicle screw into a pedicle of a patient, comprising:
  means for emitting X-rays, the means for emitting X-rays being manually positionable in more than three degrees of freedom and including a means for inserting a pedicle screw into a pedicle of a patient along an axis of operation;
  means for detecting the X-rays, the means oriented generally along a plane, the X-rays oriented along an axis parallel to the axis of operation, and generating an original image of a region of interest between the means for emitting X-rays and the means for detecting X-rays that includes the pedicle, wherein the axis of operation is positionable to an axis other than a perpendicular arrangement to the plane of the means for detecting X-rays;
  means for generating data representative of the position and orientation of the means for emitting X-rays in the more than three degrees of freedom, the means utilizing a computer processing means;
  wherein the computer processing means is operably connected to the means for detecting the X-rays and the means for generating data representative of the position and orientation of the means for emitting X-rays, the computer processing means configured to execute a means for providing a corrected image from the original image, the original image of the pedicle being skewed when the means for emitting X-rays is at an angle that is not perpendicular to the means for detecting X-rays relative to an actual appearance of the pedicle from the angle and the corrected image showing the actual appearance of the pedicle; and
  means for displaying the corrected image in real-time to a surgeon performing an operation to insert the pedicle screw into the pedicle of the patient, the means for displaying the corrected image in real-time to a surgeon performing an operation to insert the pedicle screw into the pedicle of the patient being linked to the computer processing means.

15. The system of claim 14, wherein the means for providing a corrected image executed by the computer processing means operates directly on texture coordinates of the original skewed image detected by the means for detecting using matrix transforms.

16. The system of claim 14, wherein the means for providing a corrected image executed by the computer processing means utilizes rasterization to provide the corrected image.

17. The system of claim 14, wherein the means for generating data representative of the position and orientation of the means for emitting X-rays is a kinematic or mechanical tracking system.

18. The system of claim 17, wherein the means for emitting X-rays is connected to an arm of the kinematic or mechanical tracking system.

19. The system of claim 14, wherein the means for generating data representative of the position and orientation of the means for emitting X-rays is an optical tracking system.

20. The system of claim 14, wherein the means for generating data representative of the position and orientation of the means for emitting X-rays is at least partially located within the means for emitting X-rays.

21. The system of claim 14, wherein the means for emitting X-rays is manually positionable in at least five degrees of freedom.

22. The system of claim 14, wherein the axis of operation of the means for inserting a pedicle screw and the axis along which the X-rays are emitted are coaxial.

23. The system of claim 22, wherein at least a portion of the means for inserting a pedicle screw that is coaxial with the axis along which the X-rays are emitted is formed of an X-ray translucent material.

* * * * *